United States Patent
Lai

(10) Patent No.: US 10,420,510 B2
(45) Date of Patent: Sep. 24, 2019

(54) SYSTEM AND METHOD FOR IMAGING A MOVING SUBJECT

(71) Applicant: GENERAL ELECTRIC COMPANY, Schenectady, NY (US)

(72) Inventor: Peng Lai, Menlo Park, CA (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 566 days.

(21) Appl. No.: 15/135,652

(22) Filed: Apr. 22, 2016

(65) Prior Publication Data
US 2017/0303860 A1 Oct. 26, 2017

(51) Int. Cl.
| A61B 5/055 | (2006.01) |
| A61B 5/00 | (2006.01) |
| A61B 5/0402 | (2006.01) |
| A61B 5/08 | (2006.01) |

(52) U.S. Cl.
CPC .......... *A61B 5/7207* (2013.01); *A61B 5/055* (2013.01); *A61B 5/7225* (2013.01); *A61B 5/7278* (2013.01); *A61B 5/7285* (2013.01); *A61B 5/0402* (2013.01); *A61B 5/0816* (2013.01); *A61B 2560/0223* (2013.01)

(58) Field of Classification Search
CPC ..... A61B 5/055; A61B 5/7207; A61B 5/7225; A61B 5/7285; A61B 5/0402; A61B 5/0816; A61B 2560/0223; G01R 33/4824; G01R 33/56509
See application file for complete search history.

(56) References Cited

U.S. PATENT DOCUMENTS

| 6,268,730 | B1 | 7/2001 | Du |
| 8,022,701 | B2 | 9/2011 | Chen et al. |
| 2005/0270024 | A1 | 12/2005 | Lin |
| 2013/0197347 | A1 | 8/2013 | Moghari et al. |
| 2014/0126796 | A1* | 5/2014 | Chesneau .......... G01R 33/4824 382/131 |
| 2014/0210469 | A1* | 7/2014 | Cheng .............. G01R 33/56509 324/309 |

FOREIGN PATENT DOCUMENTS

| WO | 2012-085796 A1 | 6/2012 |
| WO | 2014-165050 A1 | 10/2014 |

OTHER PUBLICATIONS

Bruno Madore et al., "Retrospectively gated cardiac cine imaging with temporal and spatial acceleration", 2011, Magnetic Resonance Imaging, 29, p. 457-469.*

(Continued)

*Primary Examiner* — Tse W Chen
*Assistant Examiner* — Milton Truong
(74) *Attorney, Agent, or Firm* — Grogan, Tuccillo & Vanderleeden, LLP

(57) ABSTRACT

An MRI system for imaging a moving subject is provided. The MRI system includes a magnet assembly and an MRI controller. The magnet assembly is configured to acquire a k-space via scanning the subject. The acquired k-space includes a plurality of datum each having a motion error. The MRI controller is configured to receive the acquired k-space from the magnet assembly. The MRI controller is further configured to suppress the motion error of each datum by reconstructing the k-space via a soft gating threshold in a non-iterative manner.

15 Claims, 7 Drawing Sheets

(56) References Cited

OTHER PUBLICATIONS

Fa-Hsuan Lin et al., "Parallel Imaging Reconstruction Using Automatic Regularization", 2004, Magnetic Resonance in Medicine, 51, p. 559-567.*
International Search Report and Written Opinion for International Application No. PCT/US2017/028296 dated Aug. 18, 2017. 10 pages.

* cited by examiner

SYSTEM AND METHOD FOR IMAGING A MOVING SUBJECT

BACKGROUND

Technical Field

Embodiments of the invention relate generally to superconducting magnets and, more specifically, to a magnetic resonance imaging system and method for imaging a moving subject.

Discussion of Art

Magnetic resonance imaging ("MRI") is a widely accepted and commercially available technique for obtaining digitized visual images representing the internal structure of objects having substantial populations of atomic nuclei that are susceptible to nuclear magnetic resonance ("NMR"). Many MRI systems use superconductive magnets to scan a subject/patient via imposing a strong main magnetic field on the nuclei in the subject to be imaged. The nuclei are excited by a radio frequency ("RF") signal at characteristics NMR (Larmor) frequencies. By spatially disturbing localized magnetic fields surrounding the subject and analyzing the resulting RF responses from the nuclei as the excited protons relax back to their lower energy normal state, a map or image of these nuclei responses as a function of their spatial location is generated and displayed. An image of the nuclei responses provides a non-invasive view of a subject's internal structure.

Many MRI systems require a subject to be scanned for an extended period of time, hereinafter referred to as a "scanning time", "scanning period", and/or simply "scan", which may last for several minutes or more while data regarding the RF responses is collected. The scanning period of such MRI systems may be long enough for subjects that are alive, e.g., a patient, to undergo several respiratory cycles. Respiratory cycles, however, can potentially cause some MRI systems to suffer "motion error" which may reduce the quality of images generated from the scan. For example, in some instances, the motion error resulting from a patient's respiratory cycles may produce motion artifacts, e.g., blurring and/or "ghosting", within generated MRI images.

Accordingly, some MRI systems avoid motion error by requiring a patient to hold their breath during various parts of the scanning period to mitigate motion error resulting from the patient's respiratory cycle. Other MRI systems, hereinafter referred to as "free-breathing" MRI systems, allow a patient to breath continuously during the scanning period and utilize respiratory gating to reduce the effects of motion error. Respiratory gating, however, often requires the use of acceptance windows, i.e., designated region(s) of a respiratory cycle from which data acquired during a scan may be used to generate an image. Generally, acceptance windows function as hard-thresholds by limiting the data used to generate an image to data acquired within an acceptance window—data acquired outside of the acceptance window is often discarded.

Typically, the smaller an acceptance window becomes, the smaller the motion error in the generated image becomes. It is often the case, however, that the smaller an acceptance window becomes, the larger the discarded portion of data to the portion of data used to generate an image becomes, and as a result, the longer the scan time becomes. Accordingly, many free-breathing MRI systems must balance image quality against scanning time. As such, many free-breathing MRI systems have small acceptance windows which typically discard as much as 70% or more of the acquired data and may have scan times on the order of ten (10) minutes or more.

Additionally, the small acceptance windows and long scan times of some free-breathing MRI systems make such MRI systems sensitive to respiratory drifting and cardiac variations, which often not only increases patient discomfort, but may also reduce scan robustness. Further, many free-breathing MRI systems ignore intra-window motion corruption and/or are unable to utilize the discarded data to improve the reconstruction of k-space.

What is needed, therefore, is an improved MRI system and method for imaging a free-breathing subject.

BRIEF DESCRIPTION

In an embodiment, an MRI system for imaging a moving subject is provided. The MRI system includes a magnet assembly and an MRI controller. The magnet assembly is configured to acquire a k-space via scanning the subject. The acquired k-space includes a plurality of datum each having a motion error. The MRI controller is configured to receive the acquired k-space from the magnet assembly. The MRI controller is further configured to suppress the motion error of each datum by reconstructing the k-space via a soft gating threshold in a non-iterative manner.

In another embodiment, a method for magnetic resonance imaging a moving subject is provided. The method includes: acquiring a k-space via scanning the subject with a magnetic resonance imaging system, the k-space including a plurality of datum each having a motion error; calculating a coil weight; and reconstructing a datum of the plurality based at least in part on the coil weight and the plurality of datum. The coil weight reduces contributions to the reconstruction of the datum from datum of the plurality having motion errors that are large and increases contributions to the reconstruction of the datum from datum of the plurality having motion errors that are small.

In yet another embodiment, an MRI controller for a MRI imaging system that images a moving subject is provided. The MRI controller is configured to: direct a magnet assembly of the MRI imaging system to acquire a k-space via scanning the subject, the k-space including a plurality of datum each having a motion error; estimate a soft gating filter; construct a motion regularization matrix based at least in part on the estimated soft-gating filter; calculate a coil weight based at least in part on the constructed motion regularization matrix; and reconstruct a datum of the plurality based at least in part on the coil weight and the plurality of datum in a non-iterative manner.

DRAWINGS

The present invention will be better understood from reading the following description of non-limiting embodiments, with reference to the attached drawings, wherein below:

DETAILED DESCRIPTION

Figure 1:
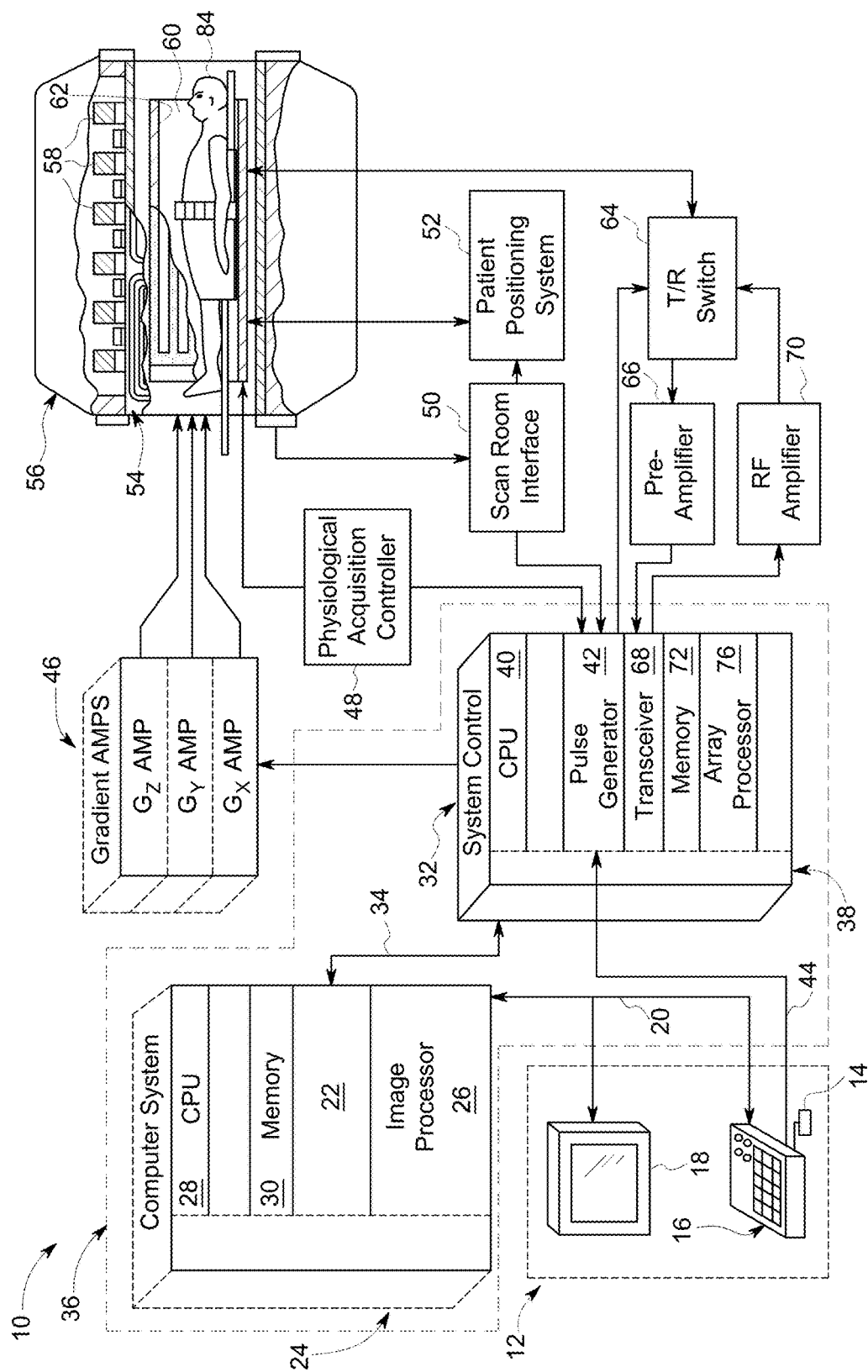
FIG. 1 is a block diagram of an exemplary MRI system in accordance with an embodiment of the invention.

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present.

Further, while the embodiments disclosed herein are described with respect to an MRI system, it is to be understood that embodiments of the present invention may be applicable to other imaging systems. Further still, as will be appreciated, embodiments of the present invention related imaging systems may be used to analyze tissue generally and are not limited to human tissue. Moreover, while embodiments of the invention are described in connection with free-breathing subjects, other embodiments may be used to compensate for other types of movement.

Referring now to FIG. 1, the major components of an MRI system 10 incorporating an embodiment of the invention are shown. Operation of the system 10 is controlled from the operator console 12, which includes a keyboard or other input device 14, a control panel 16, and a display screen 18. The console 12 communicates through a link 20 with a separate computer system 22 that enables an operator to control the production and display of images on the display screen 18. The computer system 22 includes a number of modules, which communicate with each other through a backplane 24. These include an image processor module 26, a CPU module 28 and a memory module 30, which may include a frame buffer for storing image data arrays. The computer system 22 communicates with a separate system control or control unit 32 through a high-speed serial link 34. The input device 14 can include a mouse, joystick, keyboard, track ball, touch activated screen, light wand, voice control, or any similar or equivalent input device, and may be used for interactive geometry prescription. The computer system 22 and the MRI system control 32 collectively form an "MRI controller" 36.

The MRI system control 32 includes a set of modules connected together by a backplane 38. These include a CPU module 40 and a pulse generator module 42, which connects to the operator console 12 through a serial link 44. It is through link 44 that the system control 32 receives commands from the operator to indicate the scan sequence that is to be performed. The pulse generator module 42 operates the system components to execute the desired scan sequence and produces data which indicates the timing, strength and shape of the RF pulses produced, and the timing and length of the data acquisition window. The pulse generator module 42 connects to a set of gradient amplifiers 46, to indicate the timing and shape of the gradient pulses that are produced during the scan. The pulse generator module 42 can also receive patient data from a physiological acquisition controller 48 that receives signals from a number of different sensors connected to the patient, such as ECG signals from electrodes attached to the patient. And finally, the pulse generator module 42 connects to a scan room interface circuit 50, which receives signals from various sensors associated with the condition of the patient and the magnet system. It is also through the scan room interface circuit 50 that a patient positioning system 52 receives commands to move the patient to the desired position for the scan.

The pulse generator module 42 operates the gradient amplifiers 46 to achieve desired timing and shape of the gradient pulses that are produced during the scan. The gradient waveforms produced by the pulse generator module 42 are applied to the gradient amplifier system 46 having Gx, Gy, and Gz amplifiers. Each gradient amplifier excites a corresponding physical gradient coil in a gradient coil assembly, generally designated 54, to produce the magnetic field gradients used for spatially encoding acquired signals. The gradient coil assembly 54 forms part of a magnet assembly 56, which also includes a polarizing magnet 58 (which in operation, provides a homogenous longitudinal magnetic field $B_0$ throughout a target volume 60 that is enclosed by the magnet assembly 56) and a whole-body (transmit and receive) RF coil 62 (which, in operation, provides a transverse magnetic field $B_1$ that is generally perpendicular to $B_0$ throughout the target volume 60).

The resulting signals emitted by the excited nuclei in the patient may be sensed by the same RF coil 62 and coupled through the transmit/receive switch 64 to a preamplifier 66. The amplifier MR signals are demodulated, filtered, and digitized in the receiver section of a transceiver 68. The transmit/receive switch 64 is controlled by a signal from the pulse generator module 42 to electrically connect an RF amplifier 70 to the RF coil 62 during the transmit mode and to connect the preamplifier 66 to the RF coil 62 during the receive mode. The transmit/receive switch 64 can also enable a separate RF coil (for example, a surface coil) to be used in either transmit or receive mode.

The MR signals picked up by the RF coil 62 are digitized by the transceiver module 68 and transferred to a memory module 72 in the system control 32. A scan is complete when an array of raw k-space data (74 in FIG. 3) has been acquired in the memory module 72. This raw k-space data/datum is rearranged into separate k-space data arrays for each image to be reconstructed, and each of these is input to an array processor 76 which operates to Fourier transform the data into an array of image data. This image data is conveyed through the serial link 34 to the computer system 22 where it is stored in memory 30. In response to commands received from the operator console 12, this image data may be archived in long-term storage or it may be further processed by the image processor 26 and conveyed to the operator console 12 and presented on the display 18.

Figure 2:
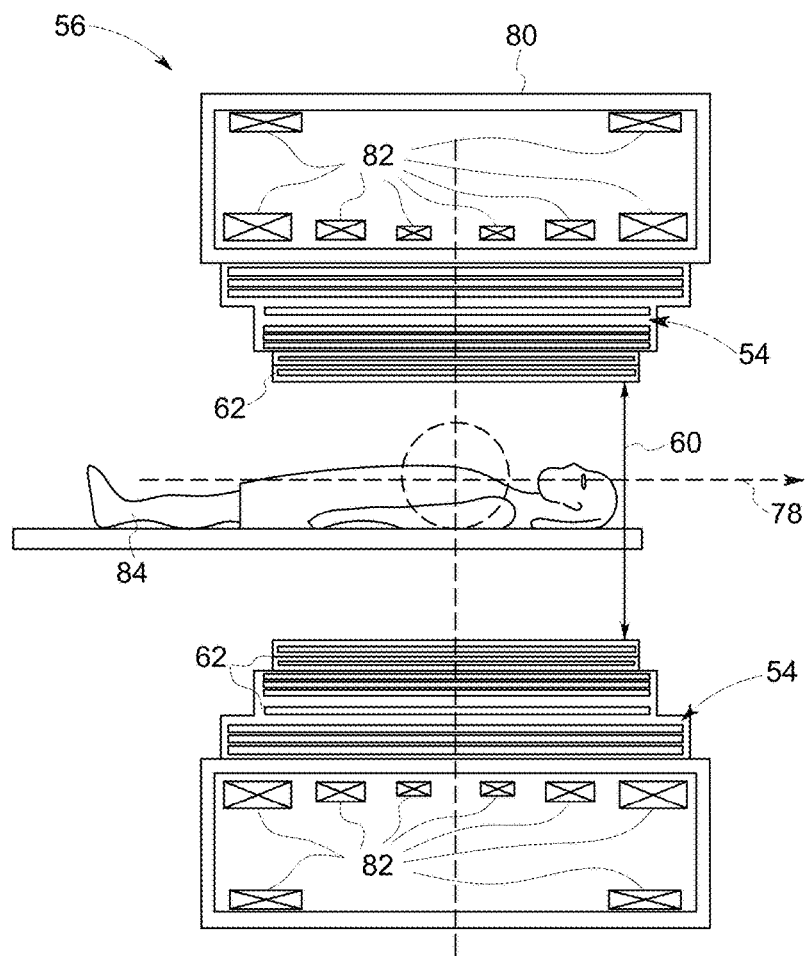
FIG. 2 is a schematic cross-sectional view of a magnet assembly of the MRI system of FIG. 1.

Referring now to FIG. 2, a schematic side elevation view of the magnet assembly 56 is shown in accordance with an embodiment of the invention. The magnet assembly 56 is cylindrical in shape having a center axis 78. The magnet assembly 56 includes a cryostat 80 and one or more radially aligned longitudinally spaced apart superconductive coils 82. The superconductive coils 82 are capable of carrying large electrical currents and are designed to create the $B_0$ field within the patient/target volume 60. As will be appreciated, the magnet assembly 56 may further include both a terminal shield and a vacuum vessel (not shown) surrounding the cryostat 80 in order to help insulate the cryostat 80 from heat generated by the rest of the MRI system (10 in FIG. 1). The magnet assembly 56 may still further include other elements such as covers, supports, suspension members, end caps, brackets, etc. (not shown). While the embodiment of the magnet assembly 56 shown in FIGS. 1 and 2 utilizes a cylindrical topology, it should be understood that topologies other than cylindrical may be used. For example, a flat geometry in a split-open MRI system may also utilize embodiments of the invention described below. As further shown in FIG. 2, a patient/imaged subject 84 is inserted into the magnet assembly 56.

Figure 3:
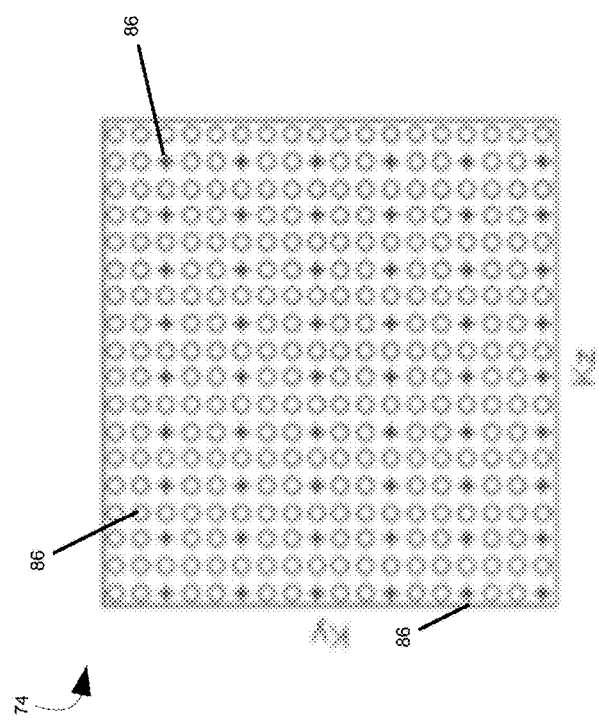
FIG. 3 is a diagram of a k-space acquired by the MRI system of FIG. 1 in accordance with an embodiment of the invention.

As illustrated in FIG. 3, in embodiments, the k-space 74 may include a plurality of datum (represented by circles/dots 86). As is to be understood, at the end of a scan, some datum 86 may be acquired (represented by the solid dots) while other datum 86 may remain unacquired (represented by the hollow dots). As used herein, an "acquired datum" is a datum 86 for which a value has been obtained, and an "unacquired datum" is a datum 86 for which a value has not been obtained. As is to be understood, a set of datum 86 may be acquired collectively as a single echo obtained by sensing a complex signal emitted by the nuclei stimulated in the subject 84 during a scanning period. Such a scanning period is referred to as readout period. As such, the set of datum acquired in a single echo forms a readout line in k-space. Accordingly, while FIG. 3 depicts the k-space 74 as two-dimensional ("2D"), it is to be understood that in reality, the k-space 74 is three-dimensional ("3D") with the readout direction perpendicular to the ky-kz plane and thus each dot or circle in the ky-kz plane is in effect a readout line. Further, while the k-space 74 shown in FIG. 3 depicts an under-sampled rate of 6, other rates may be used.

Figure 4:
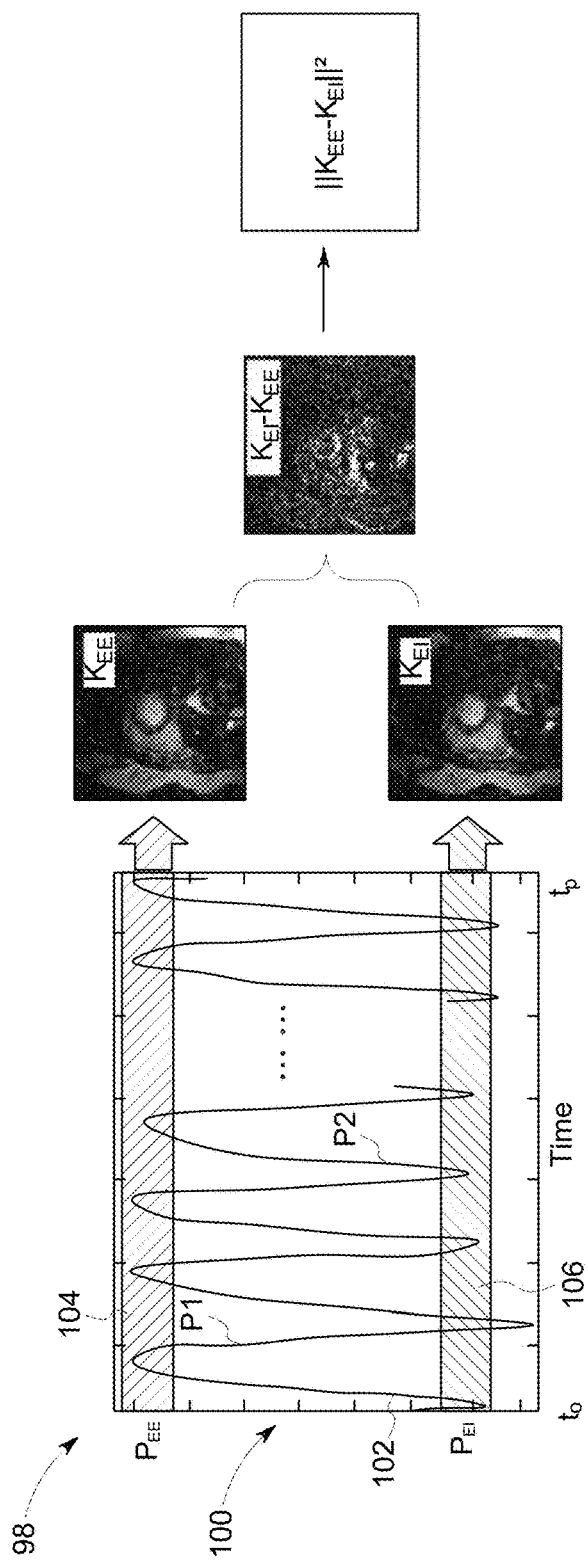
FIG. 4 is a graphical chart depicting a plurality of respiratory cycles of a subject imaged via the MRI system of FIG. 1 in accordance with an embodiment of the invention.

Turning now to FIG. 4, the MRI system 10 may be a free-breathing MRI. Accordingly, chart 98 depicts a series of respiratory cycles 100 of the subject 84 during a scanning period having start time $t_0$ and end time $t_p$. As is to be understood, line 102 represent the position of the subject 84 between an end expiration position $P_{EE}$ and an end inspiration position $P_{EI}$ at various k-space 74 acquisition/sampling/echo times. For example, points $P_1$ and $P_2$ represent acquisitions of k-space 74 near the beginning of inhalation and near the beginning of exhalation, respectively. As is to be further understood, the position 102 of the subject 84 at the end of each expiration period (shown as the peaks of line 102) may vary from one period to the next. Similarly, the position 102 of the subject 84 at the end of each inspiration period (shown as the valleys of line 102) may also vary from one period to the next. In other words, the "depths"/"sizes" of the subject's 84 breaths may vary during the scanning period. As a result, in embodiments, $P_{EE}$ and $P_{EI}$ may be a range of positions, shown as bands 104 and 106, respectively, that encompasses a range of positions that are at or near an averaged and/or reference end expiration position and averaged and/or reference end inspiration position, respectively.

As stated above, the changing position 102 of the subject 84 due to respiration during the scanning period t0 to tp may result in motion error. Accordingly, in embodiments, the datum 86 which make up the k-space 74 may each have a motion error, i.e., a variation to their value that has been induced by the motion of the subject 84 during the scan.

Figure 5:
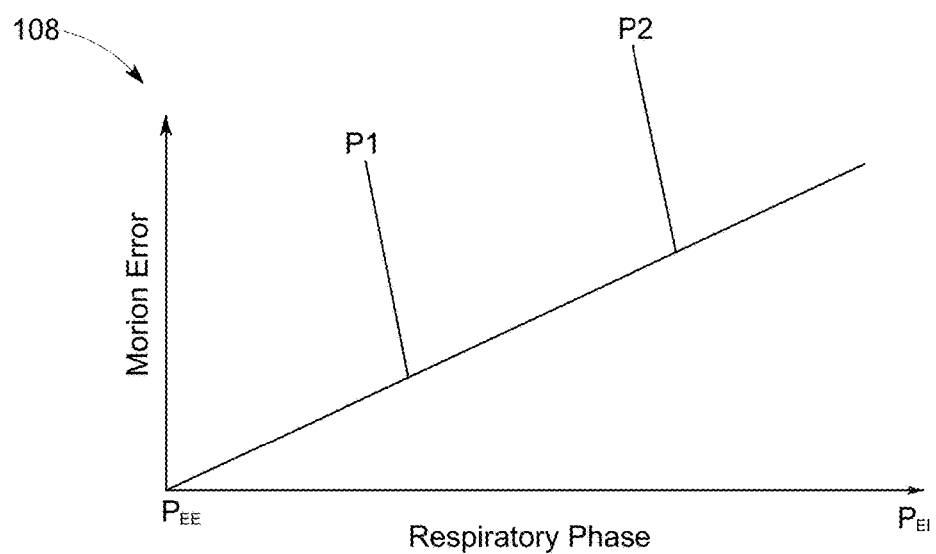
FIG. 5 is a diagram of a respiratory soft gating threshold utilized by the MRI system of FIG. 1 in accordance with an embodiment of the invention.

As shown in FIG. 5, however, the relationship between motion error and the respiratory positions/movement 102 of the subject 84 can be estimated to produce a respiratory soft gating threshold/filter 108. Therefore, as will be appreciated, in embodiments, the MRI controller 36 may be configured to suppress the motion error of each datum 86 by reconstructing the k-space 74 via the soft gating threshold 108 in a "non-iterative" manner, i.e., the MRI controller 36 can correct k-space for motion error without the need to repeat k-space acquisition via additional scans.

Figure 6:
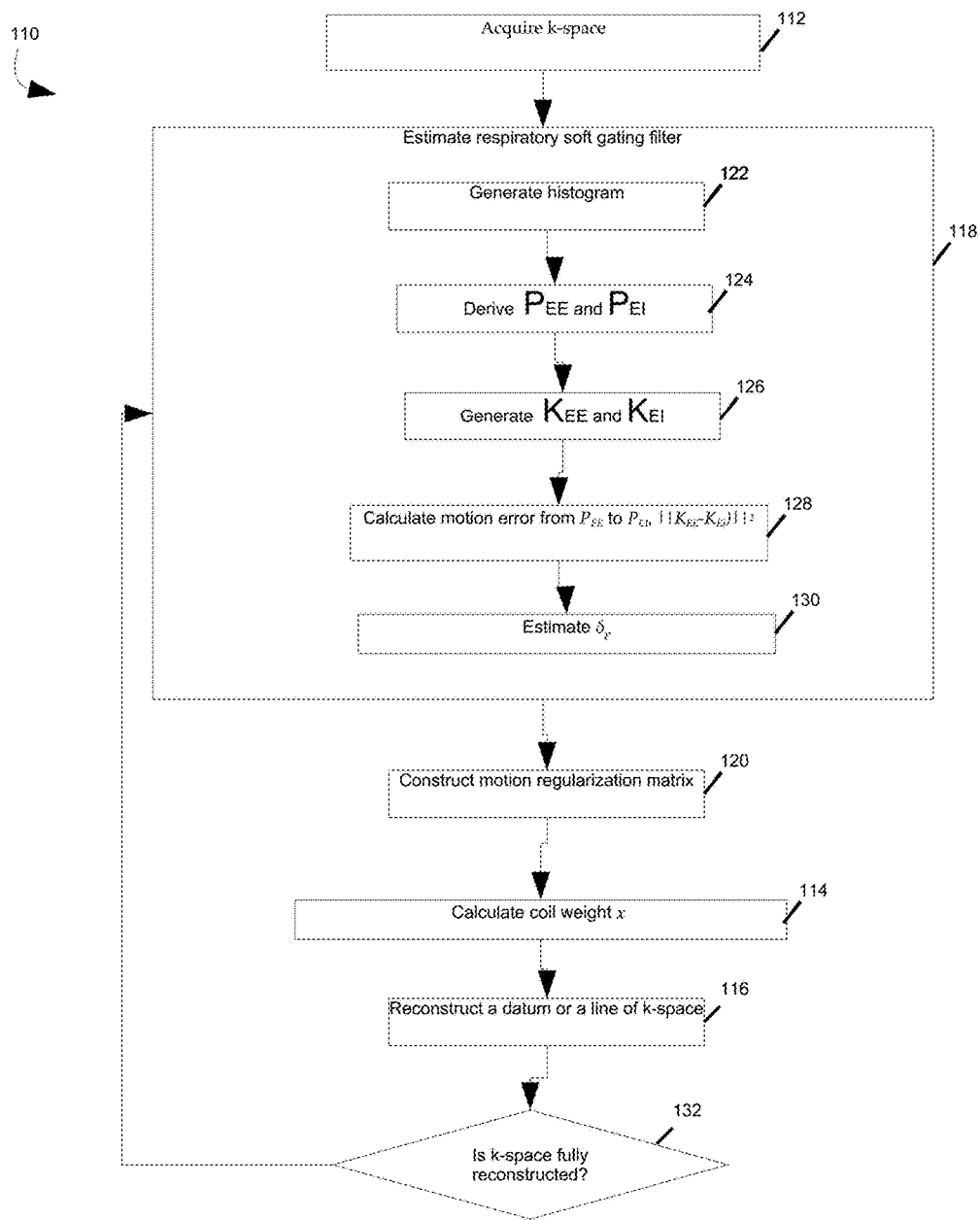
FIG. 6 is a flow chart depicting a method for magnetic resonance imaging a free-breathing subject utilizing the system of FIG. 1 in accordance with an embodiment of the invention.

Accordingly, referring now to FIG. 6, a method 110 for imaging the free-breathing subject 84 utilizing the MRI system 10 according to an embodiment is shown. As will be appreciated, in certain embodiments, an imaging application may be stored in the memory device 30, 72 which may be loaded into the CPU 28, 40 such that the MRI controller 36 is adapted by the imaging application to perform all, or part, of method 110. Accordingly, as shown in FIG. 6, the method 110 includes acquiring 112 a k-space 74 via scanning the subject 84 with the MRI system 10; calculating 114 a coil weight x; and reconstructing 116 a datum and/or a line of the plurality of datum within the acquired k-space 74 based at least in part on the coil weight x and the plurality of datum 86 of the k-space 74. As further shown in FIG. 6, in embodiments, the method 110 may further include estimating 118 the respiratory soft gating filter 108 and constructing 120 a motion regularization matrix based at least in part on the estimated soft-gating filter 108. In such embodiments, calculating 114 the coil weight x may be based at least in part on the motion regularization matrix, and the motion regularization matrix may contain values based upon the motion error of the datum 86. In embodiments, the regularization matrix may be a diagonal matrix containing motion errors of the acquired data included in a reconstruction, and each diagonal element of the regularization matrix may be equal to the motion error in the soft-gating filter corresponding to the respiratory position of an acquired datum in a reconstruction. As will also be appreciated, in embodiments, the coil weight x may be configured to reduce contributions to the reconstruction of the datum 86 an/or the line from datum 86 of the plurality having motion errors that are large and increases contribution to the reconstruction of the datum 86 and/or the line from datum 86 of the plurality having motion errors that are small. Moreover, it is to be understood that the coil weight x may be a single weight and/or a plurality of weights, e.g., a list, vectors, and/or matrix.

For example, embodiments of the invention may utilize an autocalibrating parallel imaging style method to synthesizes unacquired/target datum 86 from neighboring acquired/source datum 86 ($S_j$, j=1, 2, . . . ), i.e., one or more unacquired datum 86 may be reconstructed based on information contained by one or more acquired datum 86 that are in close proximity within k-space 74 to the one or more unacquired datum 86. The reconstruction weights, x, for a synthesis pattern may be calculated by solving:

$$Ax=b \qquad \text{(equation 1)}$$

where A and b are source and target calibration data matrixes, respectively. As such, x may be calculated by minimizing the $L_2$-norm error of:

$$\|Ax-b\|^2 \quad \text{(equation 2)}$$

As will be appreciated, the j-th column in A ($A_{.,j}$) may include concatenated calibration data with a k-space 74 shifting corresponding to $S_j$ in reconstruction. Further, in free-breathing imaging, $S_j$ may be collected with motion displacement and, accordingly, $A_{.,j}$ may need to be updated with $A_{.,j}+e_{.,j}$ to calculate the optimal x in the existence of motion, where $e_j$ represents the change in calibration data with the corresponding motion of $S_j$. Alternatively, according to equation 1, motion at $S_j$ may increase the $L_2$-norm error by $x_j\|e_{.,j}\|^2$ and the entire reconstruction error due to motion may then be approximated by $\Sigma(x_j\|e_{.,j}^2\|)$. Therefore, equation 2 turns to:

$$\min(\|Ax-b\|^2+\|\Delta x\|^2) \quad \text{(equation 3)}$$

where $\Delta$ is a diagonal matrix with $\Delta_{j,j}=\text{sqrt}(\delta_j)$ and $\delta_j=\|e_{.,j}\|^2$. As is to be further appreciated, this Tikhonov regularization has the following analytical solution:

$$x=(A^TA+\Delta^T\Delta)^{-1}A^Tb \quad \text{(equation 4)}$$

Accordingly, as can be seen, in embodiments, equation 4 reduces $x_j$ for "bad" datum 86 with large $\delta_j$ to suppress motion ($\min\|\Delta x\|^2$) and accordingly increases $x_j$ for "good" datum 86 with small $\delta_j$ to improve data fitting ($\min\|Ax-b\|^2$). For example, in embodiments datum 86 acquired at $P_1$ (shown in FIGS. 4 and 5) in the respiration cycle 100 which is close to $P_{EE}$ (and, as a result, likely to have a low motion error) may contribute more to the reconstruction than datum 86 acquired at $P_2$ (shown in FIGS. 4 and 5) which is far away from $P_{EE}$ (and therefore likely to have a high motion error).

As is to be understood, while embodiments disclosed herein utilize the coil weight x as being based on the Tikhonov regularization solution shown by equation 4, as is to be appreciated, other embodiments may utilize a coil weight x based at least in part on other Tikhonov regularization solutions, and/or a coil weight x based on a regularization method that is not a Tikhonov regularization solution, but which still ensures that the coil weight x reduces contributions to the reconstructed datum and/or line from datum 86 that have large motion errors and increases contributions to the reconstructed datum 86 and/or line from datum 86 that have small motion errors.

Referring now to FIGS. 4-6, the respiratory soft gating filter 108 may be based at least in part on the motion error of a respiration position 102 of the subject 84. In such embodiments, estimating 118 the respiratory soft gating filter 108 may be combined with the acquisition 112 of k-space 74. For example, embodiments of the invention may acquire/obtain 112 the k-space 74 via a free-breathing 3D cardiac CINE with k-t sampling and a pseudo-random vieworder. In such embodiments, acquisition 112 of center 10% k-space 74 may be repeated by four (4) or more times for estimating $\Delta$ (see equation 4 above). A histogram may be generated 122 from a simultaneously recorded respiratory signal, and the most consistent position near end-expiration $P_{EE}$ and end-inspiration $P_{EI}$ may then be derived 124. As shown in FIG. 4, in the repeatedly acquired 112 center k-space 74, two datasets at $P_{EE}$ ($K_{EE}$) and $P_{EI}$ ($K_{EI}$), respectively, may also be generated (126 in FIG. 6). The motion error from $P_{EE}$ to $P_{EI}$, $\|K_{EE}-K_{EI}\|^2$, may be calculated (128 in FIG. 6). As is to be appreciated, $\delta_P$ at a respiratory position, P (not shown), may then be estimated (130 in FIG. 6) as shown below:

$$\delta_P=\|K_{EE}-K_{EI}\|^2(P-P_{EE})/(P_{EI}-P_{EE}) \quad \text{(equation 5)}$$

While equation 5 assumes that $\delta_P$ increases linearly with off-$P_{EE}$ displacement, it is to be appreciated that equation 5 may be altered to incorporated scenarios where $\delta_P$ does not increases linearly with off-$P_{EE}$ displacement. As is to be further appreciated, different coil channels may sense motion differently and create different $\delta$'s, e.g., lower for elements near the subject's 84 dorsal and higher for elements near the subject's 84 chest wall. Therefore, in embodiments, $\|K_{EE}-K_{EI}\|^2$ may be calculated individually for each coil channel to generate coil-specific $\delta_P$'s.

As is to be understood, the datum and/or line that is reconstructed 116 may be an acquired datum 86 (solid dots) and/or line or an unacquired datum 86 (hollow dots) and/or line. Additionally, and as shown by decision block 132 in method 110, in embodiments, the MRI controller 36 may be configured to reconstruct multiple/additional datum 86 and/or lines within the k-space 74, such that the entirety of k-space 74 is reconstructed.

Figure 7:
FIG. 7 is a free-breathing MRI image generated by the system of FIG. 1 in accordance with an embodiment of the invention.

Accordingly, in an embodiment, the MRI system 10 may be based on a GE 3T (MR750), configured to obtain a free-breathing 3D CINE scan with an acceleration factor of 5, and/or further configured to operate at 750/450 W. As exemplary image taken by such an embodiment is shown in FIG. 7. In such an embodiment, the acquired k-space 74 may be processed via a k-t auto-calibrating parallel imaging method, kat ARC wherein static-tissue-removal may be utilized to identify and remove signals from static tissues, e.g., chest wall, dorsal, in the acquired k-space 74 to improve kat ARC at high acceleration. As such, the static tissue image may be generated from a time-projection dataset with weighted averaging based on $\delta_P$ to obtain motion-suppressed reconstruction in static tissues. Accordingly, in kat ARC, all k-space lines, including those acquired to correct motion corruption from acquisition, are synthesized based on equation 4, and $\Delta$ is constructed based on the P of each source line for each synthesis and the prior-calculated $\delta_P$. Because each k-space 74 neighborhood contains a mix of 'good' and 'bad' data/datum 86, equation 4 synthesizes each line in the entire k-space 74 with an $L_2$-norm-optimal balance between data fitting and motion suppression.

As will be appreciated, the presented reconstruction method could be generally applied to MRI systems with other types of motion, e.g., cardiac motion. As such, the presented respiratory soft gating to suppress respiratory motion can be replaced with general soft gating to suppress other types of motion.

Finally, it is also to be understood that the MRI system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the MRI system 10 may include at least one processor 28, 40 and system memory 30, 72, which may include random access memory (RAM) and read-only memory (ROM). The MRI system 10 may further include an input/output controller, and one or more data storage structures. All of these latter elements may be in communication with the at least one processor 28, 40 to facilitate the operation of the MRI system 10 as discussed above. Suitable computer program code may be provided for executing numerous functions, including those discussed above in connection with the MRI system 10 and methods disclosed herein. The computer program code may also include program elements such as an operating system, a database management system and "device drivers" that allow the MRI system 10, to interface with computer peripheral devices, e.g., sensors, a video display, a keyboard, a computer mouse, etc.

The at least one processor 28, 40 of the MRI system 10 may include one or more conventional microprocessors and one or more supplementary co-processors such as math co-processors or the like. Elements in communication with each other need not be continually signaling or transmitting to each other. On the contrary, such elements may transmit to each other as necessary, may refrain from exchanging data at certain times, and may cause several steps to be performed to establish a communication link there-between.

The data storage structures such as memory discussed herein may include an appropriate combination of magnetic, optical and/or semiconductor memory, and may include, for example, RAM, ROM, flash drive, an optical disc such as a compact disc and/or a hard disk or drive. The data storage structures may store, for example, information required by the MRI system 10 and/or one or more programs, e.g., computer program code such as the imaging application and/or other computer program product, adapted to direct the MRI system 10. The programs may be stored, for example, in a compressed, an uncompiled and/or an encrypted format, and may include computer program code. The instructions of the computer program code may be read into a main memory of a processor from a computer-readable medium. While execution of sequences of instructions in the program causes the processor to perform the process steps described herein, hard-wired circuitry may be used in place of, or in combination with, software instructions for implementation of the processes of the present invention. Therefore, embodiments of the present invention are not limited to any specific combination of hardware and software.

The program may also be implemented in programmable hardware devices such as field programmable gate arrays, programmable array logic, programmable logic devices or the like. Programs may also be implemented in software for execution by various types of computer processors. A program of executable code may, for instance, includes one or more physical or logical blocks of computer instructions, which may, for instance, be organized as an object, procedure, process or function. Nevertheless, the executables of an identified program need not be physically located together, but may include separate instructions stored in different locations which, when joined logically together, form the program and achieve the stated purpose for the programs such as preserving privacy by executing the plurality of random operations. In an embodiment, an application of executable code may be a compilation of many instructions, and may even be distributed over several different code partitions or segments, among different programs, and across several devices.

The term "computer-readable medium" as used herein refers to any medium that provides or participates in providing instructions to at least one processor 28, 40 of the MRI system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM) which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

Various forms of computer readable media may be involved in carrying one or more sequences of one or more instructions to at least one processor for execution. For example, the instructions may initially be borne on a magnetic disk of a remote computer (not shown). The remote computer can load the instructions into its dynamic memory and send the instructions over an Ethernet connection, cable line, or telephone line using a modem. A communications device local to a computing device, e.g., a server, can receive the data on the respective communications line and place the data on a system bus for at least one processor. The system bus carries the data to main memory, from which the at least one processor retrieves and executes the instructions. The instructions received by main memory may optionally be stored in memory either before or after execution by the at least one processor. In addition, instructions may be received via a communication port as electrical, electromagnetic or optical signals, which are exemplary forms of wireless communications or data streams that carry various types of information.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, an MRI system for imaging a moving subject is provided. The MRI system includes a magnet assembly and an MRI controller. The magnet assembly is configured to acquire a k-space via scanning the subject. The acquired k-space includes a plurality of datum each having a motion error. The MRI controller is configured to receive the acquired k-space from the magnet assembly. The MRI controller is further configured to suppress the motion error of each datum by reconstructing the k-space via a soft gating threshold in a non-iterative manner. In certain embodiments, the MRI controller is further configured to: estimate the soft gating threshold; construct a motion regularization matrix based at least in part on the respiratory soft gating threshold; calculate a coil weight based at least in part on the motion regularization matrix; and reconstruct a datum of the plurality based at least in part on the coil weight and the plurality of datum. In such embodiments, the coil weight reduces contributions to the reconstructed datum from datum of the plurality having motion errors that are large and increases contributions to the reconstructed datum from datum of the plurality having motion errors that are small. In certain embodiments, the estimated soft gating threshold is based at least in part on a motion error of a motion position of the subject during scanning. In certain embodiments, the reconstructed datum is acquired or unacquired. In certain embodiments, the MRI controller is further configured to reconstruct additional datum of the plurality so as to completely reconstruct the entire k-space. In certain embodiments, the calculated coil weight is further based at least in part on a Tikhonov regularization solution. In certain embodiments, the Tikhonov regularization solution is $x=(A^T A+\Delta^T \Delta)^{-1} A^T b$.

Other embodiments provide for a method for magnetic resonance imaging a moving subject. The method includes: acquiring a k-space via scanning the subject with a magnetic resonance imaging system, the k-space including a plurality of datum each having a motion error; calculating a coil weight; and reconstructing a datum of the plurality based at least in part on the coil weight and the plurality of datum. The coil weight reduces contributions to the reconstruction of the datum from datum of the plurality having motion errors that are large and increases contributions to the reconstruction of the datum from datum of the plurality having motion errors that are small. In certain embodiments, the method further includes: estimating a soft gating filter; and constructing a motion regularization matrix based at least in part on the estimated soft-gating filter. In such embodiments, calculating a coil weight is based at least in part on the motion regularization matrix. In certain embodiments, the soft gating filter is based at least in part on an estimated motion error of a motion position of the subject during scanning. In certain embodiments, the reconstructed datum of the plurality is acquired or unacquired. In certain embodiments, the method further includes reconstructing additional datum of the plurality so as to completely reconstruct the entire k-space in a non-iterative manner. In certain embodiments, calculating a coil weight is based at least in part on a Tikhonov regularization solution. In certain embodiments, the Tikhonov regularization solution is $x=(A^TA+\Delta^T\Delta)^{-1}A^Tb$.

Yet still other embodiments provide for an MRI controller for a MRI imaging system that images a moving subject. The MRI controller is configured to: direct a magnet assembly of the MRI imaging system to acquire a k-space via scanning the subject, the k-space including a plurality of datum each having a motion error; estimate a soft gating filter; construct a motion regularization matrix based at least in part on the estimated soft-gating filter; calculate a coil weight based at least in part on the constructed motion regularization matrix; and reconstruct a datum of the plurality based at least in part on the coil weight and the plurality of datum in a non-iterative manner. In certain embodiments, the coil weight reduces contributions to the reconstructed datum from datum of the plurality having motion errors that are large and increases contributions to the reconstructed datum or line from datum of the plurality having motion errors that are small. In certain embodiments, the soft gating filter is based at least in part on an estimated motion error of a motion position of the subject during scanning. In certain embodiments, the coil weight is based at least in part on a Tikhonov regularization solution. In certain embodiments, the Tikhonov regularization solution is $x=(A^TA+\Delta^T\Delta)^{-1}A^Tb$. In certain embodiments, the plurality of datum includes at least one of acquired datum and unacquired datum.

Accordingly, as will be appreciated, by utilizing a soft respiratory gating threshold/filter 108, some embodiments of the present invention utilize the available information contained within datum 86 that would be discarded by hard thresholding acceptance windows. As a result, some embodiments are able to reduce/suppress motion error from data within the acceptance window within a free-breathing MRI scan in a non-iterative manner, i.e., some embodiments can correct k-space for motion error by synthesizing datum 86 based on neighboring datum 86 without the need to fill/complete k-space via additional scans in an iterative manner. In some embodiments of the invention provide for increased motion suppression, shorter scanning times, and/or more efficient use of acquired data, than traditional free-breathing MRI systems using respiratory gating based on hard thresholding. Further, by utilizing a soft respiratory gating threshold/filter 108, some embodiments of the invention are able to account for intra-window motion error.

Moreover, embodiments of the invention may be implemented in 3D cine and 4D flow MRI systems. As will be appreciated, some embodiments enable free-breathing 3D cine MRI procedures while eliminating the need for the subject 84 to breath-hold during cardiac evaluations/imaging, and/or significantly improve the quality of 4D flow anatomy imagery. Accordingly, such embodiments may provide for compressive cardiac evaluations (anatomy, function, angiography, and/or flow) utilizing a single 4D flow scan.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are are not intended to be interpreted based on 35 U.S.C. § 112(f), unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A magnetic resonance imaging ("MRI") system for imaging a moving subject, the MRI system comprising:
    a magnet assembly configured to acquire a k-space via scanning the moving subject, the acquired k-space including a plurality of datum each having a motion error;
    an MRI controller configured to:
    receive the acquired k-space from the magnet assembly;
    synthesize unacquired k-space based on the acquired k-space via a soft gating threshold in a non-iterative manner, each datum in the unacquired k-space being synthesized from neighboring acquired k-space datum; and
    reconstruct an image from the acquired k-space and the synthesized unacquired k-space.

2. The MRI system of claim 1, wherein synthesizing unacquired k-space comprises:
    estimating the soft gating threshold;
    constructing a motion regularization matrix based at least in part on the soft gating threshold;
    calculating coil weights based at least in part on the motion regularization matrix; and
    synthesizing the unacquired k-space based at least in part on the coil weight and the plurality of datum of the acquired k-space;
    wherein the coil weight for a particular datum of the acquired k-space decreases as the motion error of the particular datum increases.

3. The MRI system of claim 2, wherein the estimated soft gating threshold is based at least in part on a motion error of a motion position of the moving subject during scanning.

4. The MRI system of claim 2, wherein the calculated coil weights are further based at least in part on a Tikhonov regularization solution.

5. The MRI system of claim 4, wherein the Tikhonov regularization solution is $x=(A^TA+\Delta^T\Delta)^{-1}A^Tb$.

6. A method for magnetic resonance imaging ("MRI") a moving subject, the method comprising:
    acquiring a k-space via scanning the moving subject with a MRI system, the k-space including a plurality of datum each having a motion error;
    calculating coil weights;
    synthesizing unacquired k-space based on the acquired k-space in a non-iterative manner based on the coil weights, each datum in the unacquired k-space being synthesized from neighboring acquired k-space datum; and
    reconstructing an image from the acquired k-space and the synthesized unacquired k-space;
    wherein the coil weight for a particular datum of the acquired k-space decreases as the motion error of the particular datum increases.

7. The method of claim 6, wherein synthesizing unacquired k-space further comprises:
    estimating a soft gating filter;
    constructing a motion regularization matrix based at least in part on the estimated soft-gating filter; and
    calculating the coil weights based at least in part on the motion regularization matrix.

8. The method of claim 7, wherein the soft gating filter is based at least in part on an estimated motion error of a motion position of the moving subject during scanning.

9. The method of claim 6, wherein calculating coil weights is based at least in part on a Tikhonov regularization solution.

10. The method of claim 9, wherein the Tikhonov regularization solution is $x=(A^TA+\Delta^T\Delta)^{-1}A^Tb$.

11. A magnetic resonance imaging ("MRI") controller for a MRI system that images a moving subject, the MRI controller configured to:
    direct a magnet assembly of the MRI system to acquire a k-space via scanning the moving subject, the acquired k-space including a plurality of datum each having a motion error;
    estimate a soft gating filter;
    construct a motion regularization matrix based at least in part on the estimated soft-gating filter;
    calculate coil weights based at least in part on the constructed motion regularization matrix;
    synthesize unacquired k-space based on the acquired k-space in a non-iterative manner based on the coil weights, each datum in the unacquired k-space being synthesized from neighboring acquired k-space datum; and
    reconstruct an image from the acquired k-space and synthesized unacquired k-space.

12. The MRI controller of claim 11, wherein the coil weight for a particular datum of the acquired k-space decreases as the motion error of the particular datum increases.

13. The MRI controller of claim 11, wherein the soft gating filter is based at least in part on an estimated motion error of a motion position of the moving subject during scanning.

14. The MRI controller of claim 11, wherein the coil weight is based at least in part on a Tikhonov regularization solution.

15. The MRI controller of claim 14, wherein the Tikhonov regularization solution is $x=(A^TA+\Delta^T\Delta)^{-1}A^Tb$.

* * * * *